United States Patent [19]

Babirad et al.

[11] Patent Number: 5,314,975

[45] Date of Patent: May 24, 1994

[54] FLUORINATED ACRYLAMIDE SILANE MONOMERS AND POLYMERS

[75] Inventors: Stefan A. Babirad, St. Paul; Dean M. Moren, North St. Paul; Steven M. Heilmann, Afton; Larry R. Krepski, White Bear Lake; Jerald K. Rasmussen, Stillwater, all of Minn.

[73] Assignee: Minnesota Mining and Manufacturing Company, St. Paul, Minn.

[21] Appl. No.: 10,492

[22] Filed: Jan. 28, 1993

Related U.S. Application Data

[62] Division of Ser. No. 749,926, Aug. 26, 1991, Pat. No. 5,210,248.

[51] Int. Cl.$^5$ .............................................. C08F 26/00
[52] U.S. Cl. .................... 526/248; 526/279; 526/312
[58] Field of Search ...................... 526/248, 279, 312

[56] References Cited

U.S. PATENT DOCUMENTS

| | | | |
|---|---|---|---|
| 2,743,297 | 4/1956 | Husted | 260/561 |
| 3,249,461 | 5/1966 | Te Grotenhuis | 117/76 |
| 3,997,604 | 12/1976 | Foulletier | 260/561 N |
| 4,742,177 | 5/1988 | Yamamoto et al. | 556/419 |
| 4,861,908 | 8/1989 | Satoh et al. | 556/420 |
| 4,931,582 | 6/1990 | Heilmann et al. | 560/172 |
| 4,960,844 | 10/1990 | Singh | 556/420 X |
| 4,990,641 | 2/1991 | Kabeta | 516/419 |
| 4,997,966 | 3/1991 | Lohmann et al. | 556/420 |
| 5,147,957 | 9/1992 | Kumar | 528/15 |

FOREIGN PATENT DOCUMENTS

| | | |
|---|---|---|
| 0367583 | 5/1990 | European Pat. Off. . |
| 0411666 | 8/1990 | European Pat. Off. . |

OTHER PUBLICATIONS

E. P. Pleuddeman, "Silane Coupling Agents", Plenum Press: New York, 1982, p. 20.

S. Sterman et al., "Theory of Mechanisms of Silane Coupling Agents in Glass Reinforced and Filled Thermoplastic and Thermosetting Resin Systems", Union Carbide Corporation, New York.

"A Guide to Dow Corning Silane Coupling Agents", Dow Corning Corporation, 1985, pp. 2-13.

*Primary Examiner*—John C. Bleutge
*Assistant Examiner*—Mark D. Sweet
*Attorney, Agent, or Firm*—Gary L. Griswold; Walter N. Kirn; Lorraine R. Sherman

[57] ABSTRACT

The present invention provides novel fluorinated acrylamide silane monomers which are useful as adhesion promoting agents in optical fiber cladding compositions. Polymerization of the novel monomers, optionally in the presence compatible ethylenically-unsaturated monomers, provides homopolymers and copolymers which are useful as non-wetting agents.

10 Claims, No Drawings

FLUORINATED ACRYLAMIDE SILANE MONOMERS AND POLYMERS

This is a division of application Ser. No. 07/749,926 filed Aug. 26, 1991 now U.S. Pat. No. 5,210,248.

FIELD OF THE INVENTION

This invention relates to novel fluorinated, acrylamide silane monomers, homopolymers and copolymers thereof, and a process therefor. The monomers are useful adhesion-promoting components in cladding compositions that are curable by actinic radiation and can be used to surround or cover a siliceous or polymeric core to provide an optical fiber or waveguide. The homopolymers and copolymers are useful as non-wetting agents.

BACKGROUND OF THE INVENTION

Silane coupling agents having ambifunctionality are known in the art to provide a stable bond between two dissimilar substrates, usually organic to inorganic, such as organic polymers to inorganic substrates, e.g., glass, mineral fillers, metals, and metallic oxides. The bond between the inorganic and organic components generally results in greater strength and service life to the polymer.

Polymerizable silane coupling agents are commercially available from numerous sources. Despite their general availability, however, only nonfluorinated hydrocarbon materials are known. The polymerizable group contains either (meth)acrylate, allyl, styryl, amino, or epoxy functionalities, while the silane group is usually an alkoxy silyl moiety (generally methoxy or ethoxy) which serves as a binding site to hydroxy-functional inorganic substrates via displacement of the alkoxy groups. Additional information concerning silane coupling agents may be found in the book by E. P. Pleuddeman ("Silane Coupling Agents", Plenum Press: New York, 1982, p 20-23 and 97), as well as in technical reports by S. Sterman and J. G. Marsden entitled "Theory of Mechanisms of Silane Coupling Agents in Glass Reinforced and Filled Thermoplastic and Thermosetting Resin Systems", Union Carbide Corporation, New York, and "A Guide to Dow Corning Silane Coupling Agents", Dow Corning Corporation, 1985, pp 2-13.

Substitution of fluorine for hydrogen in polymers and coatings is often desirable to impart useful properties such as lower surface energy. Typically, incorporation of fluorine into polymers and coatings has been made by copolymerizing (meth)acrylate monomers derived from (meth)acrylic acid and highly fluorinated alcohols. However, (meth)acrylates often polymerize at slow rates and provide polymers which possess inadequate thermal and hydrolytic stabilities.

Fluorinated (meth)acrylamide monomers have been described in several patents. U.S. Pat. Nos. 2,743,297 and 3,997,604 disclose fluorinated (meth)acrylamide monomers prepared by the reaction of fluorinated secondary or primary amines and (meth)acryloyl chloride. A complication in the synthesis is the removal of by-product hydrogen chloride.

2-Alkenyl azlactones are known to react with certain nucleophiles such as primary amines and alcohols to afford (meth)acrylamide-functional products. It has been disclosed in U.S. Pat. No. 4,931,582 that linear fluorinated-alcohols and -diols when reacted with 2-alkenyl azlactones yield desirable fluorinated acrylamide monomers.

It is believed that the reaction of a hydroxy-functional fluorinated acrylamide and an isocyanatoalkylsilane to afford fluorinated acrylamide silane monomers of the invention has not been previously reported.

SUMMARY OF THE INVENTION

Briefly, the present invention provides novel fluorinated acrylamide silane monomers and homo- and copolymers prepared therefrom.

The fluorinated acrylamide silane monomers are prepared by a two-step process. The initial reaction involves 2-alkenyl azlactones reacting with fluorinated diols to afford a hydroxy-functional fluorinated acrylamide. The second step involves the reaction of the aforementioned hydroxy-functional compound with an isocyanatoalkylsilane to yield fluorinated acrylamide silane monomers of the invention. The reactions are efficient and lack formation of side-products. The reaction products provide for high adhesion between a siliceous surface, i.e., a silicon based glass, and an organic polymer coating containing the polymerized fluorinated acrylamide silane of the invention, as would be useful, for example, to secure a cladding material to a siliceous core in a fiber optics construction.

Novel polymeric compositions that are useful as claddings for optical fibers are the free radical polymerization products of coating compositions which are disclosed in assignee's copending patent application U.S. Ser. No. 07/750,092 now U.S. Pat. No. 5,239,026. filed the same date as this application, which is incorporated herein by reference.

In this application:

"acrylamide" and "acrylate" are used in a generic sense and mean not only derivatives of acrylic acid, but also methacrylic and other modified acrylic acids including both so-called acryloyl, i.e., 2-propenoyl, and methacryloyl, i.e., 2-methyl-2-propenoyl, amine and alcohol derivatives, respectively;

"alkyl" and "alkylene" mean the monovalent and divalent residues remaining after removal of one and two hydrogen atoms, respectively, from a linear or branched chain hydrocarbon having 1 to 20 carbon atoms;

"lower alkyl" means $C_1$ to $C_4$ alkyl;

"aryl" and "arylene" mean the monovalent and divalent residues remaining after removal of one and two hydrogen atoms, respectively, from an aromatic compound (single ring and multi- and fused-rings) having 5 to 12 ring atoms and includes substituted aromatics such as lower alkaryl and aralkyl, lower alkoxy, N,N-di(-lower alkyl)amino, nitro, cyano, halo, and lower alkyl carboxylic ester, wherein "lower" means $C_1$ to $C_4$;

"azlactone" means 2-oxazolin-5-ones of Formula I and 2-oxazin-6-ones of Formula II:

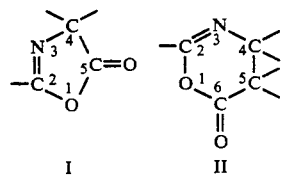

I        II

"cycloalkyl" and "cycloalkylene" mean the monovalent and divalent residues remaining after removal of one and two hydrogen atoms, respectively, from a cyclic hydrocarbon having 3 to 12 carbon atoms;

"substantially perfluorinated" means hydrocarbon groups in which at least 50 percent of the hydrogen atoms have been replaced by fluorine;

"core" means a fibril, a grating, a surface, or any other solid medium through which optical information can be transmitted;

"catenary" means in the backbone; and

"relatively optically transparent" means having an optical loss value of no more than 1000 decibels (dB) per kilometer (km).

The fluorinated acrylamide silane monomers of the present invention exhibit high rates of free radical homo- and copolymerization and yield toughened polymers compared to those resulting from corresponding acrylate- or methacrylate-functional monomers. The acrylamide functionality also offers other advantages as a polymerizable group compared to an acrylate. For instance, the amide group is known to be more difficult to hydrolyze than an ester group, and amide-functional polymers therefore are more environmentally stable. Despite these advantages, fluorinated acrylamide silane monomers have not been reported.

DETAILED DESCRIPTION OF PREFERRED EMBODIMENTS

The present invention provides a new class of polymerizable fluorinated acrylamide silane monomers preferably having general Formula III below:

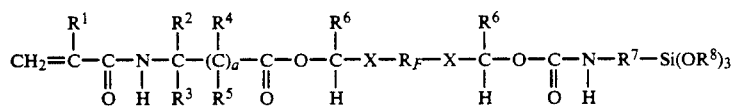

wherein:

$R^1$ and $R^6$ are independently hydrogen or methyl;

$R^2$ and $R^3$ independently can be an alkyl, preferably methyl, cycloalkyl, or aryl group, or $R^2$ and $R^3$ taken together with the carbon to which they are joined can form a carbocyclic ring containing 4 to 12 ring atoms;

$R^4$ and $R^5$ are independently hydrogen or lower alkyl;

$R^7$ can be alkylene, cycloalkylene, or arylene;

$R^8$ can be hydrogen or lower alkyl, preferably ethyl or methyl;

a is 0 or 1;

X is a carbon-to-carbon single bond, $CH_2$, $CH_2OCH_2$, or $CH_2CH_2OCH_2$; and $R_F$ is a substantially perfluorinated alkylene, cycloalkylene, or arylene group, optionally comprising up to 6 catenary non-peroxidic oxygen atoms;

The overall process, including a subsequent free radical polymerization sequence is illustrated in Chemical Scheme I below, in which preferred reactants such as 2-vinyl-4,4-dimethyl azlactone (VDM) and 1H,1H,7H,7H-tetrahydroperfluoro(2-methyl-3-oxaheptane)-1,7-diol are used to illustrate the process by which the fluorinated acrylamide silane monomers are prepared.

In the initial reaction (step A) a 2-alkenyl azlactone (Formula IV)

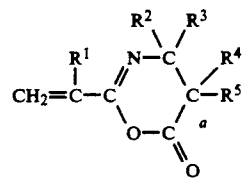

wherein $R^1$, $R^2$, $R^3$, $R^4$, $R^5$, and a are as previously defined, reacts with a fluorinated diol having the general Formula V:

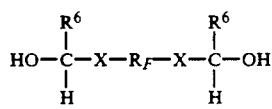

wherein:

$R_F$, $R^6$, and X are as previously described, to yield a hydroxy-functional fluorinated acrylamide of Formula VI,

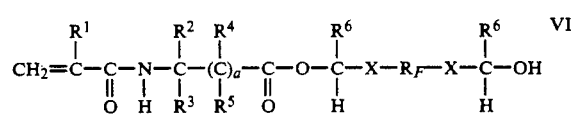

wherein:

$R^1$, $R^2$, $R^3$, $R^4$, $R^5$, $R^6$, X, $R_F$ and a are as previously described.

In a second step, condensation of the hydroxy-functional fluorinated acrylamide with an isocyanatoalkylsilane provides a fluorinated acrylamide silane monomer of the invention having general Formula III.

In a third step (step C) the fluorinated acrylamide silane monomer is polymerized through the carbon-carbon double bond to provide units of a homopolymer.

Chemical Scheme I

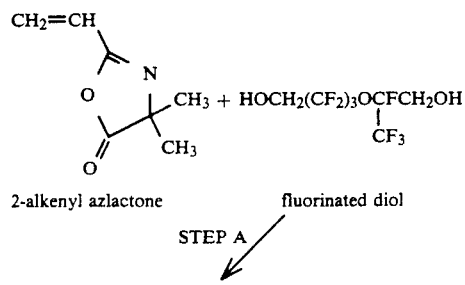

2-alkenyl azlactone         fluorinated diol

STEP A

Chemical Scheme I

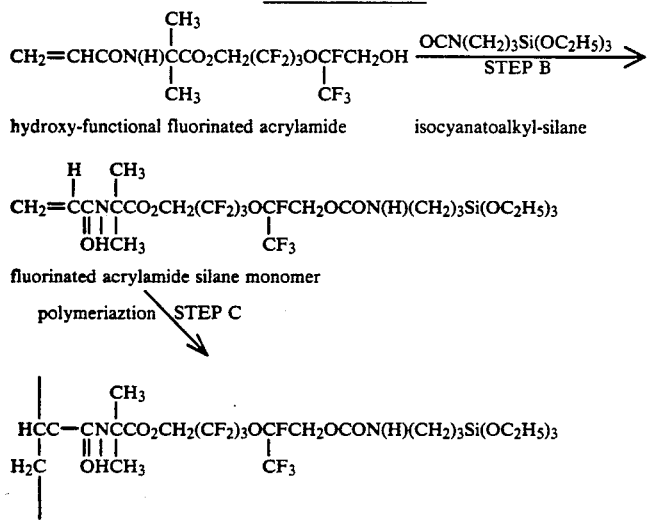

hydroxy-functional fluorinated acrylamide    isocyanatoalkyl-silane fluorinated acrylamide silane monomer polymeriaztion STEP C Useful 2-alkenyl azlactones for the present invention include: 2-vinyl-4,4-dimethyl-2-oxazolin-5-one, 2-isopropenyl-4,4-dimethyl-2-oxazolin-5-one, 2-vinyl-4-ethyl-4-methyl-2-oxazolin-5-one, 2-vinyl-4,4-diethyl-2-oxazolin-5-one, 2-vinyl-4-methyl-4-phenyl-2-oxazolin-5-one, 2-isopropenyl-4,4-tetramethylene-2-oxazolin-5-one, 2-vinyl-4,4-pentamethylene-2-oxazolin-5-one, and 2-vinyl-4,4-dimethyl-2-oxazin-6-one. The preferred 2-alekyl azlactone, because of its reactivity and commercial availability, is 2-vinyl-4,4-dimethyl-2-oxazolin-5-one (SNPE, Inc. Princeton, N.J.).

Useful fluorinated diols in the present invention include:
(1) 2,2-difluoro-1,3-propanediol,
(2) 2,2,3,3-tetrafluoro-1,4-butanediol,
(3) 2,2,3,3,4,4-hexafluoro-1,5-pentanediol,
(4) 2,2,3,3,4,4,5,5-octafluoro-1,6-hexanediol,
(5) 2,2,3,3,4,4,5,5,6,6-decafluoro-1,7-heptanediol,
(6) 2,2,3,3,4,4,5,5,6,6,7,7-dodecafluoro-1,8-octanediol,
(7) 1H,1H,7H,7H-tetrahydro-perfluoro[2-methyl-3-oxa-heptane]-1,7-diol, and
(8) 1H,1H,8H,8H-tetrahydro-perfluoro[2-methyl-3-oxa-octane]-1,8-diol.

The preferred fluorinated diol because of its reactivity is 1H,1H,7H,7H-tetrahydro-perfluoro[2-methyl-3-oxa-heptane]-1,7-diol. Compounds (1) through (7) are commercially available from Minnesota Mining and Manufacturing Company, St. Paul, Minn. Compound (8) can be prepared as described in U.S. Pat. No. 3,574,770, Example 1. Other fluorinated diols useful in the invention, especially when low melting acrylamide reaction products are desired, are those described in U.S. Pat. No. 4,906,792, which is incorporated herein by reference.

The reaction of a 2-alkenyl azlactone and a fluorinated diol (step A above) to prepare the hydroxy-functional fluorinated acrylamide monomer, is facilitated by the presence of a catalyst. Useful catalysts include 1,8-diazabicyclo[5.4.0]undec-7-ene (DBU), 1,5-diazabicyclo[4.3.0]non-5-ene (DBN), 1,4-diazabicyclo[2.2.2]octane (DABCO), triethylamine, tripropylamine, tributylamine, trihexylamine, trioctylamine, and tridecylamine. These compounds are commercially available from Aldrich Chemical Co., Milwaukee, Wis. Polymeric-supported catalysts such as those described by Tomoi in *Makromol. Chem.*, 1984, 185, 2117, can also be employed as useful catalysts.

Ion-exchange resins can also be employed as catalysts; examples include Amberlite ™ IRA-68 ion exchange resin (available from Rohm & Haas, Philadelphia, Pa.); Amberlite ™ IRA-938 ion exchange resin, Amberlite ™ IRA-400 ion exchange resin, Amberlite ™ IRA-401 S ion exchange resin, and Amberlite ™ IRA-410 ion exchange resin (available from Mallinckrodt Specialty Chemicals Co., Paris, Ky.). Concentrations of the catalysts range from 0.1 to 20 weight percent, preferably 0.25 to 5.0 weight percent, and most preferably 0.5 to 2.0 weight percent based on the azlactone reactant; triethylamine and Amberlite ™ IRA-68 ion exchange resin are preferred.

In a typical procedure, equal molar quantities of 2-alkenyl azlactone and fluorinated diol are mixed with the catalyst in the absence of solvent. Alternatively, organic solvents may be employed with the proviso that they not react with the azlactone or catalyst under the reaction conditions. Suitable organic solvents include ethyl acetate, toluene, tetrahydrofuran (available from Aldrich Chemical Co., Milwaukee, Wis.), and solvents such as Freon ™ 113 fluorinated solvent (available from E. I. Dupont de Nemours & Co., Wilmington, Del.). Especially with the preferred catalysts and a solvent-free reaction solution, a mildly exothermic reaction will ensue, and the reaction is generally complete as determined by infrared spectroscopy when the reaction temperature returns to ambient. With other catalysts and when solvents are employed, warming the reaction mixture will hasten completion of the reaction. Suitable warming temperatures are from 40°–80° C.; preferably 40°–65° C., for a period of 0.5 to 12 hours, preferably 0.5 to 2 hours.

In the case of ion-exchange resins, the catalyst may be efficiently removed from the reaction product by filtration. The catalyst may be rejuvenated by washing the ion exchange resin with alkali and drying. Other catalysts may be removed from the reaction product by distillation.

It is generally advisable to add a free radical stabilizer such as phenothiazine or 2,6-di-t-butyl-p-cresol in concentrations by weight based on reaction product from 0.001 to 1.0 percent, preferably 0.05 to 0.15 percent.

Useful isocyanatoalkylsilanes in the present invention include 2-isocyanatoethyltrimethoxysilane, 3-isocyanatopropyltrimethoxysilane, 2-isocyanatoethyltriethoxysilane, and 3-isocyanatopropyltriethoxysilane, with 3-isocyanatopropyltriethoxysilane (available from Petrarch Systems, Bristol, Pa.) being preferred. Reactions may take place at ambient temperature. In a typical procedure, equal molar quantities of the above prepared hydroxy-functional fluorinated acrylamide and isocyanatoalkylsilane are mixed in the absence of solvent. Alternatively, organic solvents, as noted above, may be employed with the proviso that they not react with the reactants under the reaction conditions. The condensation reaction is enhanced in the presence of minor amounts, i.e. 0.01 to 1.0 weight percent, of a catalyst. Suitable catalysts are tertiary amines and metal salts or complexes of organic compounds. Examples of tertiary amines include: N,N-dimethylaminoethanol, N,N-dimethylcyclohexylamine, diaminobicyclooctane (DABCO), and N,N'-diethylpiperazine. Examples of metal salts or complexes of organic compounds include: stannous octoate, dibutyltin dilaurate, dibutyltin thiocarboxylates, and ferric acetylacetonate. A thorough discussion on catalyst systems can be found in the book by G. Woods "The ICI Polyurethanes Book" Wiley & Sons: New York, 1987, pp 41–45. The preferred catalyst is dibutyltin dilaurate and is available from Aldrich Chemical Co., Milwaukee, Wis.

By reason of the acrylamide functionality, novel and useful polymers of the invention are obtained by polymerization of monomers of Formula III to form homopolymers and copolymers having units of Formula VII,

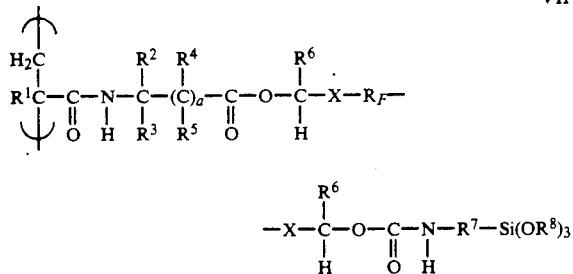

wherein $R^1$, $R^2$, $R^3$, $R^4$, $R^5$, $R^6$, $R^7$, $R^8$, $R_F$, X, and a are as previously defined, to provide the polymers with approximate molecular weights in the range of 2,000 to 5,000,000.

Copolymers can be formed from the fluorinated acrylamide silane monomers of the present invention with any compatible ethylenically-unsaturated monomer in any proportion. Copolymers are preferably prepared by mixing compatible monomers with the monomers of the invention in the presence of free radical catalysts in the presence of heat or UV irradiation as necessary to obtain the desired reaction rate. Examples include: (a) with acrylates or methacrylates such as methyl(meth)acrylate, lauryl(meth)acrylate, dodecyl(meth)acrylate, perfluorooctyl(meth)acrylate, and the like; (b) with styrenes such as styrene, alpha-methylstyrene, and parachlorostyrene; (c) with acrylamides and methacrylamides such as acrylamide, N,N-dimethylacrylamide, N-isopropylacrylamide, and N-phenylacrylamide; (d) with ethylenically-unsaturated monomers such as vinyl chloride, vinyl acetate, vinylidene fluoride, and vinyl azlactones, and (e) with allyl derivatives, such as diallyl phthalate, triallyl cyanurate, and the like. Preferably the copolymer contains at least 0.25 percent by weight of the fluorinated acrylamide silane monomer in the invention and preferably at least 5.0 weight percent up to 99 weight percent. Copolymers of the invention can be used as non-wetting agents.

As is known to those skilled in the art, when monomers of the invention form copolymers, units selected from the above structures and comonomer units may react in any proportion and will be distributed throughout the polymer in a more or less random fashion depending upon the comonomer and the degree of similarity of its polymerization kinetics to the monomer of Formula III.

Polymerization of the monomers may be carried out by employing initiators which generate free radicals on application of activating energy as is conventionally used in the polymerization of ethylenically-unsaturated monomers. Included among useful free radical initiators are thermally activated initiators such as organic peroxides, organic hydroperoxides, and azo compounds. Representative examples of such initiators include benzoyl peroxide, tertiary-butyl perbenzoate, diisopropyl peroxydicarbonate, cumene hydroperoxide, azobis(isobutyronitrile), and the like. Generally, from about 0.1 to 10 percent by weight of thermal initiator is used.

Actinic radiation may be utilized to initiate polymerization. High energy electrons emitted from commercial electron beam generators are commonly employed in these ionizing radiation systems. Photoinitiators may also be employed to initiate polymerization. Such initiators are well known and have been described in the polymerization art, e.g., Chapter II of "Photochemistry" by Calvert and Pitts, John Wiley and Sons (1966). Preferred photoinitiators are those which facilitate polymerization when the composition is irradiated with ultraviolet light. Representative examples of such initiators include acyloin and derivatives thereof, such as benzoin, benzoin ethyl ether, benzoin isopropyl ether, alpha-methylbenzoin; diketones such as benzil, and diacetyl, etc.; ketones such as acetophenone, methyl benzoylformate, 2-hydroxy-2-methyl-1-phenyl-1-propanone, benzophenone, and the like. Normally, the photoinitiator is used in amounts ranging from about 0.001 to 10 percent by weight of the total monomeric composition. Preferably, about 0.05 to 1.0 percent of photoinitiator is used in the polymerizable compositions.

When the activating energy is only heat, polymerization is usually carried out at a temperature in the range of 40° to 140° C. for about 5 to 48 hours. It is to be understood that polymerization conditions are not limited to the stated temperature or time conditions, nor is initiation limited to use of ultraviolet radiation or heat alone, but combination may be employed as well.

The novel fluorinated acrylamide silane monomers of the invention provide novel claddings for siliceous cores and transparent organic polymer cores and substrates which are useful for transmitting optical information. These compositions are disclosed in the aforementioned U.S. Ser. No. 07/750,092, now U.S. Pat. No. 5,239,026 which is incorporated herein by reference.

Representative polymer cores and supports include poly(methyl methacrylate), poly(styrene), and poly(carbonates). The cladding materials are the free radical polymerization products of the above-referenced coating compositions selected to provide a refractive index lower than that of the core, preferably at least 0.03 units less, more preferably at least 0.05 units less than the refractive index of the core. Typically cores have diameters in the range of 100 to 1000 micrometers, and claddings can range in thickness from 5 to 100 micrometers. The cladding compositions may also comprise a thermal stabilizer/antioxidant.

The monomers of the invention are useful as adhesion-promoting components in cladding compositions for optical fibers. Information transfer using a modulated light beam guided by optical fibers can have applications, for example, in telecommunications and computer link-ups. Due to the increase of numerical aperture (NA), other applications such as laser delivery systems where real time sensing capabilities are feasible with the cladding compositions of the present invention. These optical fiber linkages have advantages compared to metal wires carrying electrical signals in that they have very high information carrying capacities and are free from external interferences, such as electromagnetic interference.

The monomers of the invention can be polymerized to form homopolymers and copolymers which are useful as non-wetting agents.

Objects and advantages of this invention are further illustrated by the following examples, but the particular materials and amounts thereof recited in these examples, as well as other conditions and details, should not be construed to unduly limit the invention.

EXAMPLE 1

This Example teaches preparation of a fluorinated acrylamide silane monomer in accordance with the scheme below:

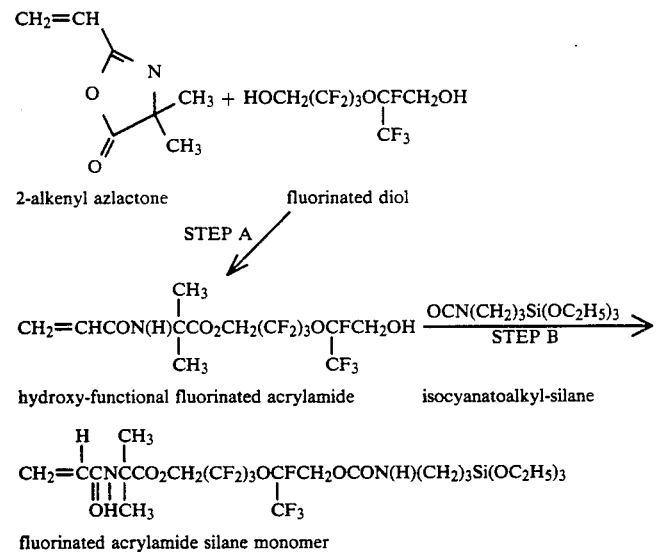

Step A: 1H,1H,7H,7H-tetrahydro-perfluoro(2-methyl-3-oxa-heptane)-1,7-diol (available from Minnesota Mining & Manufacturing, St. Paul, Minn.) (41.05 grams, 0.125 mole) and 2-vinyl-4,4-dimethylazlactone (VDM) (SNPE, Inc., Princeton, N.J.) (17.41 grams, 0.125 mole) were mixed to provide a homogeneous solution. To this solution was added dry Amberlite TM IRA-68 polymeric resin (Rohm & Haas, Philadelphia, Pa.) (3.00 grams, 5.6 meq/gram). The reaction mixture was then shaken for five hours at room temperature and thirty hours at 70° C. An infrared spectrum showed characteristic absorptions for the acrylamide product. The crude product was dissolved in a solvent mixture of chloroform and Freon TM 113 fluorinated solvent (E.I. Dupont de Nemours & Co., Wilmington, Del.) (5:1) (250 mL), and the insoluble polymeric resin was filtered. The filtrate was treated with water (30 mL) containing 5 drops of trifluoroacetic acid and stirred overnight. The contents of the flask were poured into a separatory funnel. The organic layer was separated, dried over anhydrous magnesium sulfate, and filtered. The filtrate was concentrated using a rotary evaporator to leave the desired hydroxy-functional fluorinated acrylamide.

Step B: In a one-necked 250 mL round-bottomed flask, were added the product from Example 1 (24.27 grams, 0.052 mole) and 3-isocyanatopropyltriethoxysilane (Petrarch Systems, Bristol, Pa.) (12.85 grams, 0.052 mole). The mixture was stirred at room temperature under a nitrogen atmosphere and treated with 2 drops of dibutyltin dilaurate (Aldrich Chemical Co., Milwaukee, Wis.). The reaction mixture was allowed to stir an additional 16 hours at which time spectral analysis confirmed the presence of the desired fluorinated acrylamide silane monomer.

Similarly, using fluorinated diols designated (1) through (8) above, other alkenyl azlactones mentioned above, and other isocyanatoalkylsilanes mentioned above, a variety of fluorinated acrylamide silane monomers can be prepared.

EXAMPLE 2

This example teaches the use of copolymers containing fluorinated acrylamide silanes as claddings components for optical fibers. A monomeric cladding composition was prepared using the fluorinated acrylamide silane from Example 1, as follows:

| Monomers | |
|---|---|
| (perfluorocyclohexyl) methyl acrylate (3M, St. Paul, MN) | 91.0 grams |
| fluorinated diacrylate (prepared as in U.S. Pat. No. 3,055,932, Example 1) | 5.0 grams |
| fluorinated acrylamide silane (from Example 1) | 2.0 grams |
| Darocur TM initiator 1173 (E. M. Merck | 2.0 grams |

-continued

| Monomers |
| --- |
| Industries, Hawthorne, NY) |

The apparatus for producing the optical fiber was a 6.7 meter (22 foot) Astro Tower equipped with an Astro Graphite Resistance Furnace (available from the Astro Division of Thermal Technologies, Santa Rosa, Calif.). The glass core material emanated from a Diasil Preform Rod (available from Mitsubishi Rayon Co., Ltd., Tokyo, Japan), and the coating station, where the cladding composition was applied, was an open cup design. Ultraviolet actinic radiation was supplied by a medium pressure mercury lamp, and irradiation of the coated monomeric cladding composition to provide a copolymer took place in an atmosphere of nitrogen; the optical fiber was produced at a constant speed of 20 meters/minute.

A 600 meter length of the optical fiber consisting of a 200 micrometer glass core and a 25 micrometer clad was overcoated with a Tefzel ™ 210 fluorinated polymeric buffer coating (E. I. Dupont de Nemours, Wilmington, Del.) by coextrusion. The principle of overcoating an optional fiber with Tefzel ™ 210 fluoropolymer is discussed by M. M. Ramsay in Chapter 2 of the book entitled "Fiber Optics Handbook", McGraw Hill: New York, 1989, pp 2.13–2.20. The resultant optical fiber exhibited a loss of 4.3 dB/km. The loss measurement was obtained using a Tektronix ™ 506 Optical Time Domain Reflectometer (OTDR) (available from Tektronix, Portland, Oreg.) with the loss value at 812 nm being recorded. The principle of the OTDR measurement is discussed by D. Marcuse in his book entitled "Principles of Optical Fiber Measurements", Academic Press: New York, 1981, pp 236–241, and procedures utilized were that of Electronic Industries Association Standard 455-46 (May 1983). The numerical aperture (NA) of a 2 meter length of the optical fiber was measured to be 0.46, at 633 nm. The principle of the NA measurement is discussed by D. L. Philen and W. T. Anderson in Chapter 8 of the book entitled "Optical Fiber Telecommunications II", Academic Press: New York, 1988, pp 331–332, and test methods utilized were that of Electronic Industries Association Standard 455-47 (May 1983).

EXAMPLE 3

| Monomers | |
| --- | --- |
| (perfluorocyclohexyl) methyl acrylate | 86.0 grams |
| fluorinated diacrylate (as prepared in U.S. Pat. No. 3,055,932, Example 1) | 10.0 grams |
| fluorinated acrylamide silane (from Example 1) | 2.0 grams |
| Darocur 1173 | 2.0 grams |

A 1.2 kilometer section of an optical fiber overcoated with Tefzel ™ 210 prepared as in Example 2 exhibited a loss of 3.7 dB/km. Using the procedure of Example 2 the NA measurement of this optical fiber was found to be 0.45. The strength of the fiber was determined by proof testing the fiber at $3.45 \times 10^9$ dynes/cm$^2$ (50 kpsi) without evidence of optical loss change. The principle of proof testing optical fibers is discussed by F. C. Allard in his book entitled "Fiber Optics Handbook For Engineers and Scientists", McGraw-Hill, Inc.: New York, 1990, pp 1.40–1.41 and 4.49–4.52 and test methods utilized were that of Fiber Optic Test Procedures, FOTP-31.

EXAMPLE 4

| Monomers | |
| --- | --- |
| (perfluorocyclohexyl) methyl acrylate | 83.0 grams |
| fluorinated diacrylate (as prepared in U.S. Pat. No. 3,055,932, Example 1) | 10.0 grams |
| fluorinated acrylamide silane (from Example 1) | 5.0 grams |
| Darocur 1173 | 2.0 grams |

A 1.2 kilometer section of an optical fiber overcoated with Tefzel 210 prepared as in Example 2 exhibited a loss of 4.2 dB/km. Using the procedure of Example 2 the NA measurement of this optical fiber was found to be 0.44. Using the procedure of Example 3, the strength of the fiber was determined by proof testing the fiber at $3.45 \times 10^9$ dynes/cm$^2$ (50 kpsi) without evidence of optical loss change.

EXAMPLE 5

This example teaches the use of the fluorinated acrylamide silane homopolymer of the invention as a non-wetting agent.

| Preparation of the fluorinated acrylamide silane homopolymer | |
| --- | --- |
| Charge: | |
| fluorinated acrylamide silane (from Example 1) | 14.2 grams |
| ethyl acetate | 127.4 grams |
| azobis(iso-butyronitrile) | 0.03 grams |

The charge solution was degassed for ten minutes with nitrogen in a vessel. The vessel was sealed and heated with agitation at 65° C. for 18 hours. At that point, the homopolymer solution was clear and viscous.

A portion of the homopolymer solution was applied to the surface of a clear, clean glass surface. The residual solvent was removed from the homopolymer coating by slow evaporation at room temperature. The advancing contact angle of the treated glass substrate was then measured utilizing a goneometer with Nujol and glycerol. In comparative example 6, a commercial silane, 3-(trimethyoxysilyl)propyl methacrylate, Aldrich Chemical Co., was similarly tested as a non-wetting agent. The contact angles obtained are shown in TABLE I below.

TABLE I

| | | Contact Angle | | |
| --- | --- | --- | --- | --- |
| Example | Silane tested | Nujol | Glycerol | Surface Tension (dynes/cm) |
| 6 (comparative) | commercial | 37° | 81° | 28.1 |
| 5 | invention | 48° | 103° | 23.0 |

The above data indicates that the homopolymer of Example 5 is superior to the commercial silane homopolymer in its non-wetting characteristics.

A comonomer, such as methyl (meth)acrylate, can be added to the polymerizable composition to provide a novel non-wetting agent.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A polymer comprising fluorinated acrylamide silane units, wherein said units have the formula

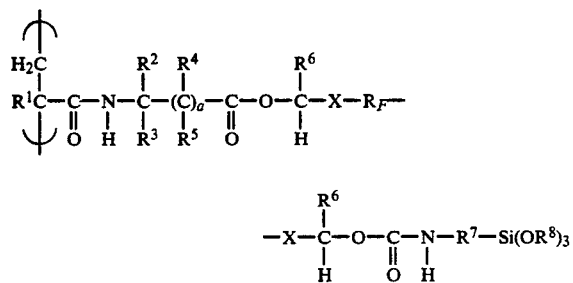

wherein $R^1$ and $R^6$ are independently hydrogen or methyl;

$R^2$ and $R^3$ independently can be an alkyl, cycloalkyl, or aryl groups, or $R^2$ and $R^3$ taken together with the carbon to which they are joined can form a carbocyclic ring containing 4 to 12 ring atoms;

$R^4$ and $R^5$ are independently hydrogen or lower alkyl;

$R^7$ is alkylene, cycloalkylene, or arylene;

$R^8$ is hydrogen or lower alkyl;

a is zero or 1;

X is a carbon-to-carbon single bond, $CH_2$, $CH_2OCH_2$, or $CH_2CH_2OCH_2$; and $R_F$ is a substantially perfluorinated alkyl, cycloalkyl, or aryl group, comprising 0 to 6 catenary non-peroxidic oxygen atoms.

2. The polymer according to claim 1 wherein $R^1$ is hydrogen.

3. The polymer according to claim 1 wherein $R^1$ is methyl.

4. The polymer according to claim 1 wherein a=zero.

5. The polymer according to claim 1 wherein $R^4$ and $R^5$ are each hydrogen.

6. The polymer according to claim 1 wherein $R^8$ is methyl, ethyl or hydrogen.

7. The polymer according to claim 1 wherein
$R^1$ is H,
$R^2$ is $CH_3$,
$R^3$ is $CH_3$,
a=0,
each $R^6$ is H,
$R_F=(CF_2)_3OCF(CF_3)$,
each X=carbon-to-carbon single bond,
$R^7=(CH_2)_3$,
$R^8=C_2H_5$.

8. The polymer according to claim 1 which is a non-wetting agent.

9. The polymer according to claim 1 which is a homopolymer.

10. The polymer according to claim 1 which is a copolymer further comprising units derived from a compatible ethylenically unsaturated monomer by copolymerization.

* * * * *

UNITED STATES PATENT AND TRADEMARK OFFICE
CERTIFICATE OF CORRECTION

PATENT NO. : 5,314,975
DATED : May 24, 1994
INVENTOR(S) : Stefan A. Babirad et al.

It is certified that error appears in the above-indentified patent and that said Letters Patent is hereby corrected as shown below:

Col. 4, lines 11-19, delete formula IV and replace it with the following: --

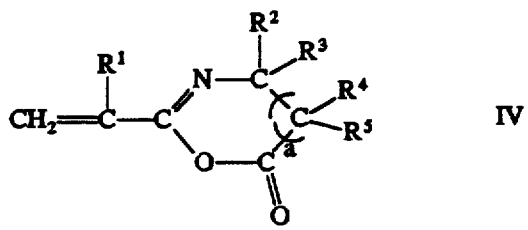

IV

--.

Col. 5, delete the final formula of the Chemical Scheme I and replace it with the following:

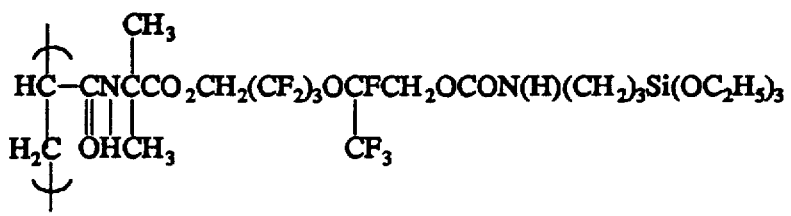

UNITED STATES PATENT AND TRADEMARK OFFICE
CERTIFICATE OF CORRECTION

PATENT NO. : 5,314,975
DATED : May 24, 1994
INVENTOR(S) : Stefan A. Babirad et al.

It is certified that error appears in the above-indentified patent and that said Letters Patent is hereby corrected as shown below:

Col. 5, line 32, "2-alekyl azlactone" should read -- 2-alkenyl azlactone --.

Col. 14, lines 10-11, "a = -zero" should read -- a = zero --.

Signed and Sealed this

Twenty-seventh Day of September, 1994

Attest:

BRUCE LEHMAN

Attesting Officer

Commissioner of Patents and Trademarks